United States Patent [19]

Muchel

[11] 4,220,401
[45] Sep. 2, 1980

[54] HAND-HELD OPHTHALMOSCOPE

[75] Inventor: Franz Muchel, Königsbronn, Fed. Rep. of Germany

[73] Assignee: Carl Zeiss Stiftung, Oberkochen, Fed. Rep. of Germany

[21] Appl. No.: 895,690

[22] Filed: Apr. 12, 1978

[30] Foreign Application Priority Data

Apr. 15, 1977 [DE] Fed. Rep. of Germany ....... 2716615

[51] Int. Cl.² .............................................. A61B 3/10
[52] U.S. Cl. ......................................... 351/13; 351/6
[58] Field of Search ..................... 351/6, 7, 10, 11, 12, 351/13, 16

[56] References Cited

U.S. PATENT DOCUMENTS

| | | | |
|---|---|---|---|
| 3,535,027 | 10/1970 | Littmann et al. | 351/14 |
| 3,572,910 | 3/1971 | Koester | 351/13 |
| 3,640,610 | 2/1972 | Nupuf | 351/13 |
| 3,776,619 | 12/1973 | Heine | 351/12 |

*Primary Examiner*—John K. Corbin
*Assistant Examiner*—Rodney Bovernick
*Attorney, Agent, or Firm*—Stonebraker, Shepard & Stephens

[57] ABSTRACT

A hand-held ophthalmoscope having a handle part and a head part, with an illuminating device in the handle part. In the head part is an imaging lens system for producing an image of the fundus of the eye being examined, and an axially displaceable optical system for focussing the image of the fundus at infinity. The illuminating device in the handle has a source of light and a condenser and a field diaphragm. There is an optical system for imaging the field diaphragm in the key of the patient. A test mark is pivotally mounted on the mount of the axially displaceable optical system in the head portion of the device, and may be moved into cooperative relation to a scale. Preferably the optical system for producing the image of the fundus, and the partial optical system for imaging the field diaphragm or the test mark, have the same focal length. Preferably also there is an image erecting prism between the optical system which serves to produce the image of the fundus and the optical system which serves to focus the image of the fundus at infinity.

7 Claims, 1 Drawing Figure

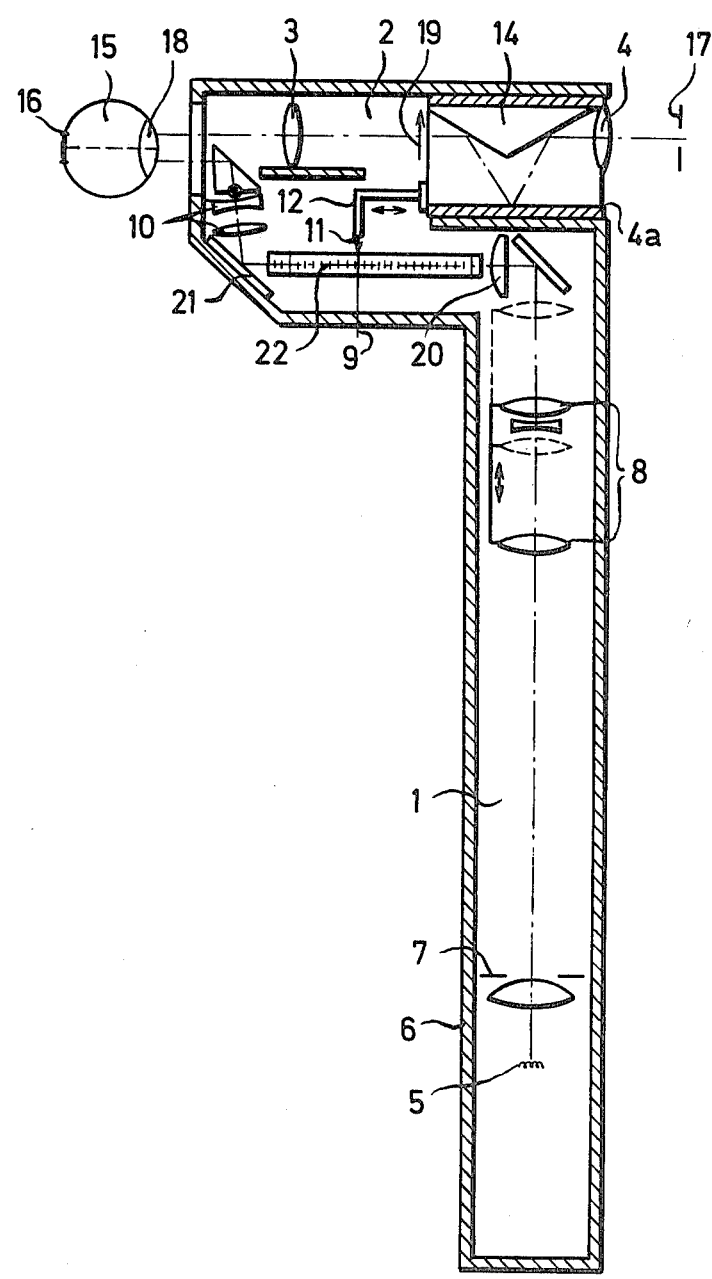

HAND-HELD OPHTHALMOSCOPE

BACKGROUND OF THE INVENTION

This invention relates to a portable ophthalmoscope adapted to be held in the hand of the user, that is, in the hand of a doctor who is examining the eye of a patient. The ophthalmoscope of the present invention comprises a handle part or portion and a head part or portion.

Various ophthalmoscopes are known in the art which, depending upon their optical design, produce either an inverted image, or an erect and laterally correct image of the eye background or retina to be examined, either for monocular or binocular viewing. The known hand ophthalmoscopes have the disadvantage that the patient's pupil and the doctor's pupil are not conjugated to each other. Because of this, a so-called keyhole effect is produced. That is, the doctor who cannot bring the pupil of his eye to the locus of the exit pupil sees a blurred limitation of the field of view, which is dependent upon the position of his eye. The field of view, as in the case of observation through a hole which is at a certain distance from the eye of an observer, can be viewed in its entirety only by successive movements of the eye of the observer.

Another disadvantage of the known forms of hand ophthalmoscope is that when the doctor has imperfect sight, additional lenses must be swung into the ray path, in order to correct for the doctor's visual deficiency, and that upon a determination of the visual deficiency of the patient, the doctor must take his own visual deficiency into account. Another disadvantage is that upon the focussing of a test mark on the retina of the patient, the position of the test mark must be displaced by means of a cam in accordance with the visual deficiency.

An object of the present invention is to avoid various disadvantages of the known forms of ophthalmoscopes, particularly the keyhole effect and the cumbersome compensation for the visual deficiency of the doctor, and to design the ophthalmoscope in such a way as to make possible a rapid and simple determination of the visual deficiency of the patient.

According to the present invention, this object is achieved by a combination of features of placing the illuminating device in the handle part of the ophthalmoscope, arranging the imaging lens system in the head part of the ophthalmoscope, and employing an imaging lens system which comprises an optical system for producing an image of the fundus or retina to be examined and an axially displaceable optical system for focussing the image of the fundus at infinity.

The illuminating device preferably comprises a source of light, and a condenser lens with a field diaphragm, and an imaging system which images the source of light and the field diaphragm into the eye of the patient. If an imaging system of variable imaging scale is introduced between the field diaphragm and the test mark, a larger field of lesser brightness or a smaller field of greater brightness can be illuminated, as desired, on the fundus.

In one advantageous embodiment of the invention, an arm which bears a test mark for determining the visual deficiency of the patient, is pivotted to the mount of the axially displaceable optical system.

It is advantageous to provide the optical system for producing the image of the fundus and the optical system for forming the image of the field diaphragm or a test mark in the eye of the patient, of the same focal length. With this arrangement, in the case of defective vision of the patient, the intermediate image plane in which the image of the fundus is produced and the image plane in which the field diaphragm is imaged are subjected to the same variation.

In order to offer the doctor an image of the fundus in the conventional manner, an image erecting prism is preferably introduced between the optical system for producing the image of the fundus and the optical system for focussing the image of the fundus at infinity.

BRIEF DESCRIPTION OF THE DRAWING

The single FIGURE is a diagrammatic or schematic representation of an ophthalmoscope in accordance with a preferred illustrative embodiment of the invention.

DESCRIPTION OF THE PREFERRED EMBODIMENT

The ophthalmoscope comprises a housing or casing having a handle part or portion 1 and a head part or portion 2, both made of any suitable material such as metal or a rigid plastic material. In the head portion is an optical system indicated schematically at 3, and a second optical system indicated schematically at 4, the latter being mounted on a frame or mount 4a which is movable in the direction of the optical axis of the optical system 4 by any conventional adjusting mechanism, such for example as a rack and pinion, or a screw thread, or any other desired mechanism.

The eye of the patient to be examined is indicated schematically at 15. The image of the fundus or retina of the eye produced by the crystalline lens 18 of the eye is focussed by the optical system 3 onto the intermediate image plane indicated schematically at 19. The pupil of the eye of the doctor who is making the examination is indicated schematically at 17. Through the optical system 4, the doctor views the image of the fundus on the image plane 19. Preferably there is an image erecting prism 14 arranged between the optical system 3 and the optical system 4, so that the doctor may view the fundus of the eye of the patient in correct orientation without having to make allowance for inversion of the image.

The patient-side focal point of the system 4 can always be brought to the locus of the image of the fundus, said locus moving in an axial direction in accordance with the condition of the eye of the patient. If the pupil of the patient is brought into the front focal point of the system 3, then the position of the exit pupil referred to the system 4 becomes independent of the position at that time of the system 4. The focal lengths of the optical systems 3 and 4 are so dimensioned that the exit pupil is so far away from the vertex of the system 4 that the use of eyeglasses by the observing doctor is possible.

In the handle portion 1 there is arranged the illumination system comprising a source of light 5 (for example, an incandescent filament powered by a battery) and a condenser lens 6 and a field diaphragm 7. From these elements, the illumination travels up the hollow handle portion to an adjustable pancratic system 8 which focusses the image of the field diaphragm 7 (after reflection and refraction as illustrated) at an intermediate plane 9. This intermediate image formed at 9 is focussed by an optical system 10 into the eye of the patient, by means of a mirror 21, and a prism which is part of the optical system 10 as illustrated. The field lens 20, through which the rays pass between the field diaphragm 7 and the image plane 9, assures a telecentric ray path, so that the image of the source of light 5 is always produced in the front focal point of the optical system 10.

If the optical system 10 is given the same focal length as the optical system 3, then the image plane 9 and the image plane 19 will be subjected to the same variation, corresponding to the visual deficiency of the patient.

A test mark 11 is adjustably mounted on the optical system 4 or on its mount 4a by means of an adjustable and swingable arm 12. This test mark 11 is read in conjunction with a scale 22. When the parts are adjusted to produce a sharp focussing of the fundus of the patient in the eye of the doctor, then it is possible to obtain a simultaneous sharp focussing of the test mark plane 9 in the eye of the patient, and the extent of the visual defect of the patient can be noted by reading the position of the test mark 11 on the scale 22.

What is claimed is:

1. An ophthalmoscope comprising a hollow handle part and a hollow head part, illuminating means at least partly in the handle part, and an imaging lens system in the head part, said imaging lens system including a first optical system (3) for producing an image of the fundus of an eye being examined and a second optical system (4) axially displaceable for focussing the image of the fundus at infinity, an image erecting prism arranged in front of said second optical system and operatively connected therewith, and a test mark operatively connected with said prism.

2. The invention defined in claim 1, wherein said illuminating means comprises a source of light (5), a condenser lens (6), a field diaphragm (7), and optical means (8, 10) for imaging the field diaphragm in the eye being examined.

3. The invention defined in claim 2, wherein said optical means (8, 10) comprises a third optical system (8) and a fourth optical system (10).

4. The invention defined in claim 3, wherein said third optical system (8) focuses an image of the field diaphragm at an intermediate plane (9), and said fourth optical system (10) focuses the image from said intermediate plane in the eye being examined.

5. The invention defined in claim 3, wherein said fourth optical system (10) has the same focal length as said first optical system (3).

6. The invention defined in claim 1, further comprising an arm (12) bearing said test mark (11), said arm being operatively connected to move with axial movements of said second optical system (4).

7. The invention defined in claim 4, wherein said test mark is mounted for movement to a position in which said fourth optical system (10) may form an image of the test mark in the eye being examined.

* * * * *